(12) United States Patent
Cho et al.

(10) Patent No.: US 9,724,018 B2
(45) Date of Patent: Aug. 8, 2017

(54) METHOD FOR MONITORING PHRENIC NERVE FUNCTION

(75) Inventors: Yong K. Cho, Maple Grove, MN (US); Scott A. Ransom, Marysville, WA (US); Xusheng Zhang, Shoreview, MN (US)

(73) Assignee: Medtronic CryoCath LP, Toronto, Ontario (CA)

( * ) Notice: Subject to any disclaimer, the term of this patent is extended or adjusted under 35 U.S.C. 154(b) by 1377 days.

(21) Appl. No.: 13/282,713

(22) Filed: Oct. 27, 2011

(65) Prior Publication Data
US 2013/0109994 A1 May 2, 2013

(51) Int. Cl.
A61B 5/08 (2006.01)
A61B 5/11 (2006.01)
A61N 1/08 (2006.01)
A61B 5/00 (2006.01)

(52) U.S. Cl.
CPC .............. *A61B 5/1104* (2013.01); *A61N 1/08* (2013.01); *A61B 5/7217* (2013.01)

(58) Field of Classification Search
None
See application file for complete search history.

(56) References Cited

U.S. PATENT DOCUMENTS

| | | | |
|---|---|---|---|
| 4,289,142 A | 9/1981 | Kearns | |
| 5,215,082 A | 6/1993 | Kallok et al. | |
| 5,540,732 A | 7/1996 | Testerman | |
| 5,707,398 A | 1/1998 | Lu | |
| 5,758,652 A | 6/1998 | Nikolic | |
| 5,782,826 A * | 7/1998 | Swanson | A61B 18/1492 606/34 |
| 5,980,463 A | 11/1999 | Brockway et al. | |
| 6,064,910 A | 5/2000 | Andersson et al. | |
| 6,085,118 A | 7/2000 | Hirschberg et al. | |
| 6,126,611 A | 10/2000 | Bourgeois et al. | |
| 6,269,269 B1 | 7/2001 | Ottenhoff et al. | |
| 6,278,894 B1 | 8/2001 | Salo et al. | |
| 6,600,949 B1 | 7/2003 | Turcott | |
| 6,641,542 B2 | 11/2003 | Cho et al. | |

(Continued)

FOREIGN PATENT DOCUMENTS

WO  2009102726 A1  8/2009

OTHER PUBLICATIONS

Franchesci et al.,Diaphragmatic electromyography during cryoballoon ablation: a novel concept in the prevention of phrenic nerve palsy, Heart Rhythm, Jun. 2011, 885-891.*

*Primary Examiner* — Michael Kahelin
*Assistant Examiner* — Tho Tran
(74) *Attorney, Agent, or Firm* — Christopher & Weisberg, P.A.

(57) ABSTRACT

Systems and methods for monitoring phrenic nerve function of a patient are disclosed, including, including establishing a diaphragmatic movement value threshold; positioning a diaphragmatic movement sensor on an external surface of an abdomen of the patient; applying a treatment regimen to a tissue region in proximity to the phrenic nerve; measuring a diaphragmatic movement value with the diaphragmatic movement sensor; comparing the measured diaphragmatic movement value to the established diaphragmatic movement value threshold; and generating an alert in response to the comparison.

8 Claims, 9 Drawing Sheets

(56) References Cited

U.S. PATENT DOCUMENTS

| | | |
|---|---|---|
| 6,752,765 B1 | 6/2004 | Jensen et al. |
| 6,772,008 B2 | 8/2004 | Zhu et al. |
| 7,025,730 B2 | 4/2006 | Cho et al. |
| 7,094,207 B1 | 8/2006 | Koh |
| 7,142,919 B2 | 11/2006 | Hine et al. |
| 7,160,252 B2 | 1/2007 | Cho et al. |
| 7,236,828 B2 | 6/2007 | Casavant et al. |
| 7,245,971 B2 | 7/2007 | Park et al. |
| 7,357,775 B1 | 4/2008 | Koh |
| 7,371,220 B1 | 5/2008 | Koh et al. |
| 7,389,140 B1 | 6/2008 | Kroll |
| 7,392,086 B2 | 6/2008 | Sathaye |
| 7,647,108 B2 | 1/2010 | Freeberg |
| 2006/0149328 A1 | 7/2006 | Parikh et al. |
| 2006/0241708 A1 | 10/2006 | Boute |
| 2007/0027488 A1 | 2/2007 | Kaiser et al. |
| 2007/0055124 A1 | 3/2007 | Viswanathan et al. |
| 2007/0118183 A1 | 5/2007 | Gelfand et al. |
| 2007/0179544 A1 | 8/2007 | Kuehn |
| 2008/0161657 A1 | 7/2008 | Bullens et al. |
| 2009/0043352 A1* | 2/2009 | Brooke et al. ................. 607/28 |
| 2009/0054742 A1* | 2/2009 | Kaminska ............ A61B 5/0002 600/301 |
| 2009/0182318 A1* | 7/2009 | Abboud et al. ................ 606/21 |
| 2010/0121406 A1* | 5/2010 | Libbus et al. ................. 607/42 |
| 2010/0241113 A1* | 9/2010 | Ingle .............................. 606/21 |
| 2010/0305637 A1 | 12/2010 | McCabe et al. |
| 2010/0305638 A1 | 12/2010 | McCabe et al. |
| 2010/0305647 A1 | 12/2010 | McCabe et al. |
| 2011/0098761 A1* | 4/2011 | Wittenberger et al. ........... 607/1 |
| 2011/0105921 A1* | 5/2011 | Wang ............................ 600/508 |
| 2012/0290036 A1* | 11/2012 | Karamanoglu et al. ........ 607/42 |
| 2013/0030498 A1* | 1/2013 | Karamanoglu ...... A61N 1/3611 607/42 |

* cited by examiner

Heart: Anterior Exposure

METHOD FOR MONITORING PHRENIC NERVE FUNCTION

CROSS-REFERENCE TO RELATED APPLICATION n/a

STATEMENT REGARDING FEDERALLY SPONSORED RESEARCH OR DEVELOPMENT n/a

FIELD OF THE INVENTION

The present invention relates to methods and systems for monitoring and preventing unintended nerve injury during a medical procedure.

BACKGROUND OF THE INVENTION

When treating particular regions of tissue, through thermal energy interaction or the like for example, it may be difficult to direct or control the depth and intensity of the heat transfer. The delivery of thermal energy or other therapeutic modality, such as radiofrequency or cryogenic applications, may not necessarily be contained to the exact region or depth desired for treatment, as the tissue may have varying therapy-conducive properties affected by the surrounding physiological environment. While thermal control or precision may be of more concern with certain treatment modalities, such as radiofrequency, microwave, and/or cryogenic treatment procedures, it is often desirable to limit thermal treatment or exposure to just the tissue desired. Failure to do so may otherwise negatively and adversely affect surrounding tissue structures or organs that are sensitive and susceptible to undesired damage.

For example, when attempting to treat cardiac tissue, sensitive tissue structures abound that may react adversely to thermal applications. In particular, when thermally treating or ablating tissue in or about the heart, it is essential that critical physiological structures such as the phrenic nerve, sinoatrial node, and the like are not inadvertently destroyed through such ablation therapy. The phrenic nerve is made up mostly of motor nerve fibers that produce contractions of the diaphragm and thus affect breathing and respiration patterns and conditions. In addition, the phrenic nerve provides sensory innervation for many components of the mediastinum and pleura, as well as the upper abdomen, especially the liver, and the gall bladder.

The phrenic nerve is generally referred to in two segments: the right and left phrenic nerves. Both phrenic nerves run from C3, C4 and C5 vertebrae along the anterior scalene muscle deep to the carotid sheath. The right phrenic nerve passes over the brachlocephalic artery, posterior to the subclavian vein, and then crosses the root of the right lung anteriorly and then leaves the thorax by passing through the vena cava hiatus opening in the diaphragm at the level of T8. The right phrenic nerve passes over the right atrium. The left phrenic nerve passes over the pericardium of the left ventricle and pierces the diaphragm separately.

Referring to FIGS. 1-3, the close proximity of the phrenic nerve segments to the right atrium and left ventricle is illustrated. These cardiac regions may be the location or origin of heart arrhythmias or other physiological maladies and thus targeted for tissue ablation in order to remove or otherwise remedy the abnormal electrophysiological occurrence. In thermally treating or ablating select cardiac regions, the phrenic nerve may be at risk of being similarly, although unintentionally, ablated. This could severely impact the normal respiratory functioning of the patient. Such injury can manifest as a transient phrenic functional block, transient phrenic nerve palsy (PNP), or longer-term phrenic nerve injury. These injuries reduce respiratory function and can require many weeks or months to resolve. In the worst cases, this reduced function requires mechanical ventilation assistance to maintain respiration. As such, the risk of such unintentional and undesirable destruction or application of thermal energy to this and other cursory structures compels a desire to monitor or otherwise detect potentially-damaging consequences during treatment.

Such monitoring is typically performed using one of two methods: 1) pacing the phrenic nerve and using continuous fluoroscopy during the ablation to visualize a consistent diaphragmatic response; or 2) palpation of the abdomen to confirm diaphragmatic movement. Both methods require vigilance on the part of the operator, and can distract the physician from the main focus of the diagnostic or treatment procedure at hand. Further, in the case of fluoroscopic monitoring, the patient is exposed to increased x-ray radiation.

Accordingly, it is desirable to provide systems and methods for automated monitoring of phrenic nerve function that would reduce physician distraction, reduce procedure fluoroscopy time, and ensure timely identification of transient injury, leading to prevention of long-term phrenic injury.

SUMMARY OF THE INVENTION

The present invention advantageously provides methods and systems to monitor or otherwise detect potentially-damaging consequences during treatment of sensitive tissue areas, such as the phrenic nerve. For example, a method of monitoring phrenic nerve function of a patient is disclosed, including establishing a diaphragmatic movement value threshold; positioning a diaphragmatic movement sensor on the patient so as to detect diaphragmatic movement; applying a treatment regimen to a tissue region in proximity to the phrenic nerve; measuring a diaphragmatic movement value with the diaphragmatic movement sensor; comparing the measured diaphragmatic movement value to the established diaphragmatic movement value threshold; and generating an alert in response to the comparison. Establishing the diaphragmatic movement value threshold may include pacing the phrenic nerve and measuring a diaphragmatic movement value in response to the pacing; and the diaphragmatic movement value threshold may include a range of values. The diaphragmatic movement sensor may include one or more accelerometers and the diaphragmatic movement value may include the rate of a single thoracic excursion, an amplitude of a thoracic excursion, and/or a quantity of thoracic excursions occurring within a predetermined time period. The method may include adjusting the treatment regimen in response to the comparison, and the treatment regimen may include ablating cardiac tissue.

A method of monitoring phrenic nerve function of a patient is also disclosed, including establishing an acoustic diaphragm contraction value threshold; positioning an acoustic sensor on an external surface of the patient in proximity to a diaphragm of the patient; applying a treatment regimen to a tissue region in proximity to the phrenic nerve; measuring an acoustic value corresponding to diaphragm contraction; comparing the measured acoustic value to the established acoustic diaphragm contraction value threshold; and generating an alert based at least in part on the comparison. Establishing the acoustic diaphragm contraction value threshold may include pacing the phrenic nerve and measuring an acoustic value corresponding to diaphragm contraction in response to the pacing. The acoustic sensor may include a microphone and/or an accelerometer. The method may include establishing a diaphragm electromyogram threshold; obtaining an electromyogram of the diaphragm; comparing the obtained electromyogram to the established diaphragm electromyogram threshold; and/or generating an alert based at least in part on the comparison.

A medical system is provided, including a motion sensor positionable on an exterior surface of a patient; a controller in communication with the motion sensor, the controller programmed to: calculate at least one of a slope or an amplitude of a diaphragm excursion based on a signal received from the motion sensor; compare the at least one of the slope or the amplitude to a predetermined threshold; and generate an alert based on the comparison. The motion sensor may include a plurality of accelerometers and/or the alert may include at least one of an audible or visual alert. The system may include a tissue treatment device in communication with the controller, where the controller is programmed to modify operation of the tissue treatment device based at least in part on the comparison.

BRIEF DESCRIPTION OF THE DRAWINGS

A more complete understanding of the present invention, and the attendant advantages and features thereof, will be more readily understood by reference to the following detailed description when considered in conjunction with the accompanying drawings wherein.

DETAILED DESCRIPTION OF THE INVENTION

Figure 1:
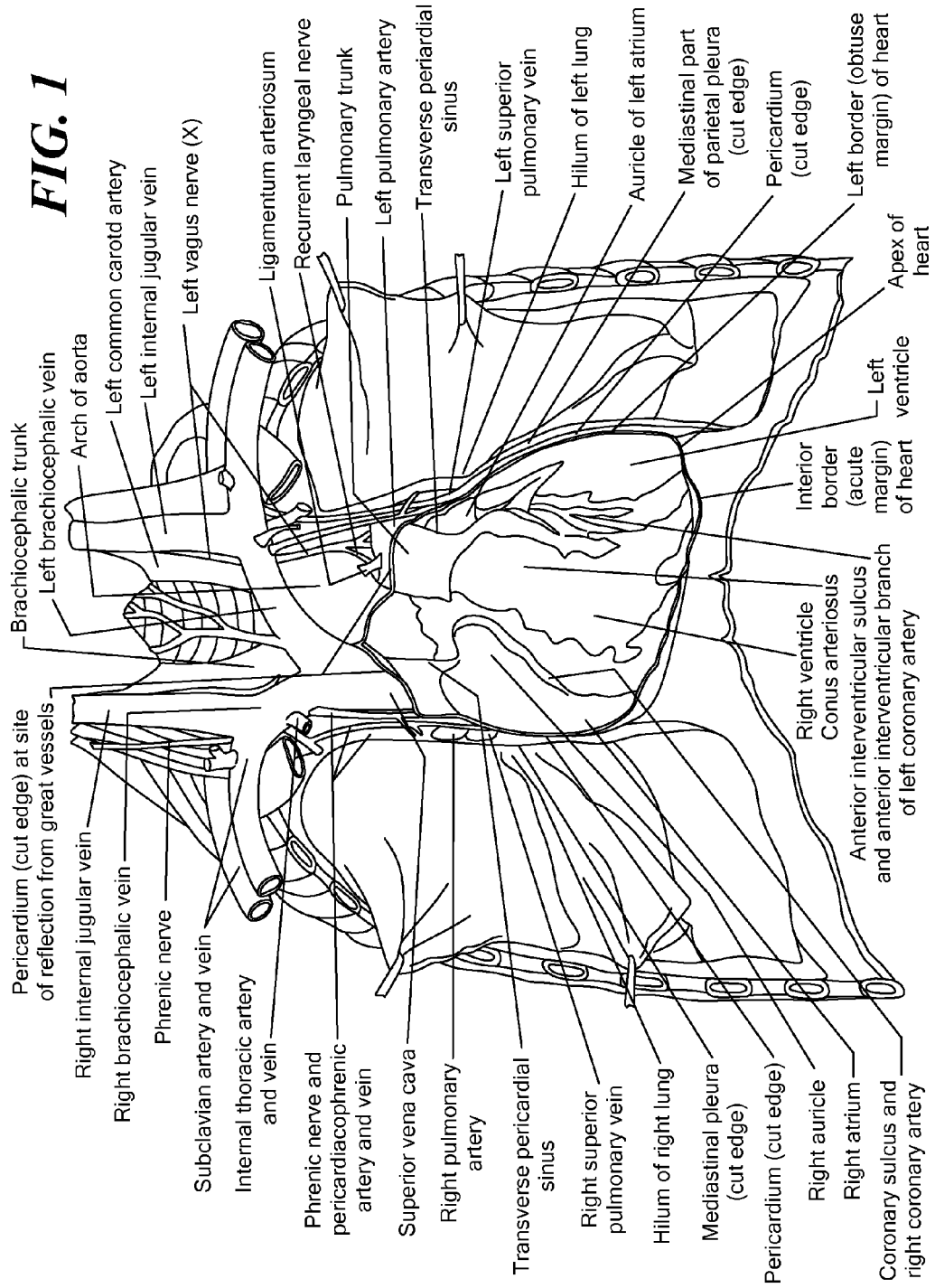
FIG. 1 is an anterior illustration of a thoracic region and related anatomy.
Figure 2:
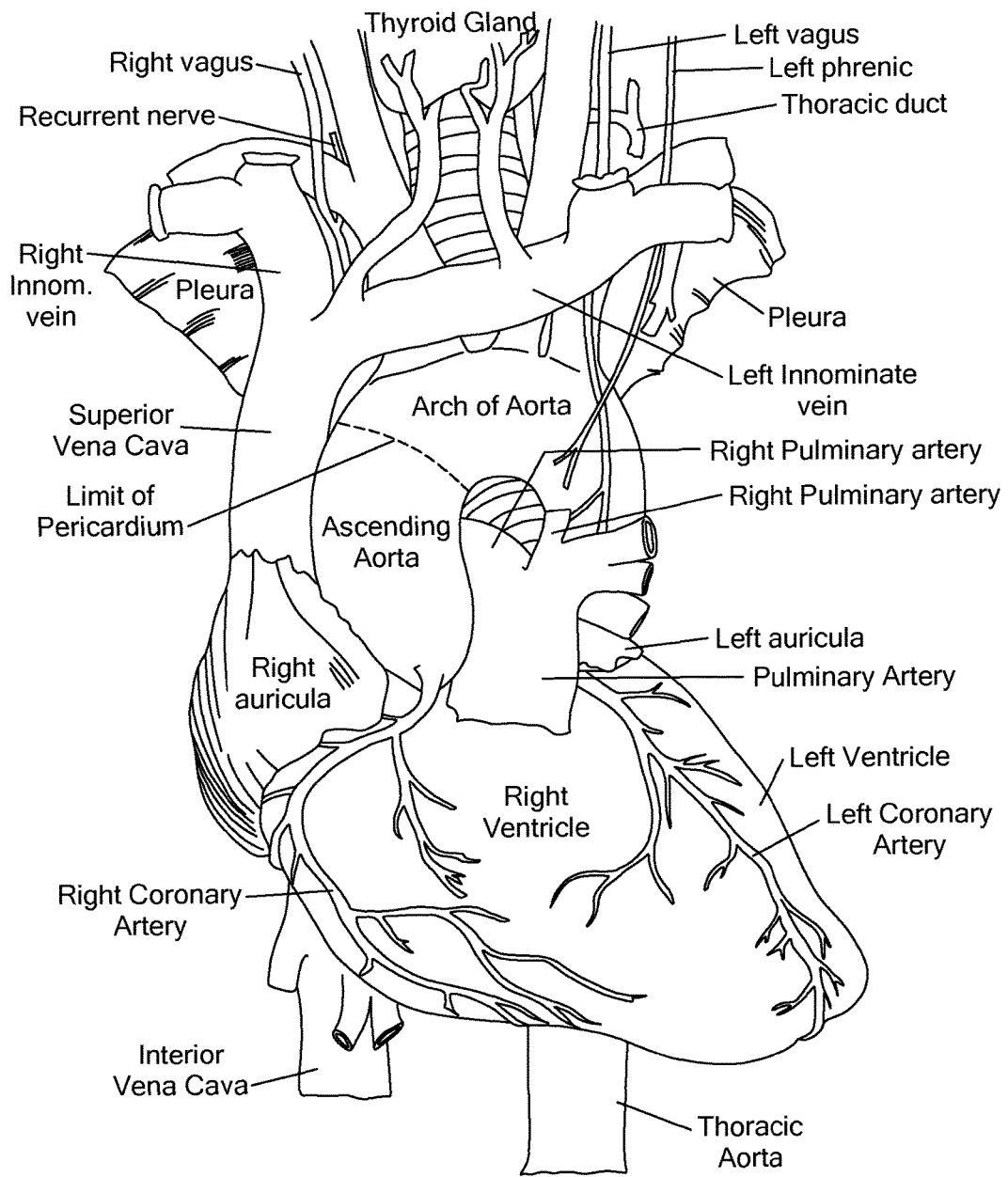
FIG. 2 is an illustration of a human heart and related anatomy.
Figure 3:
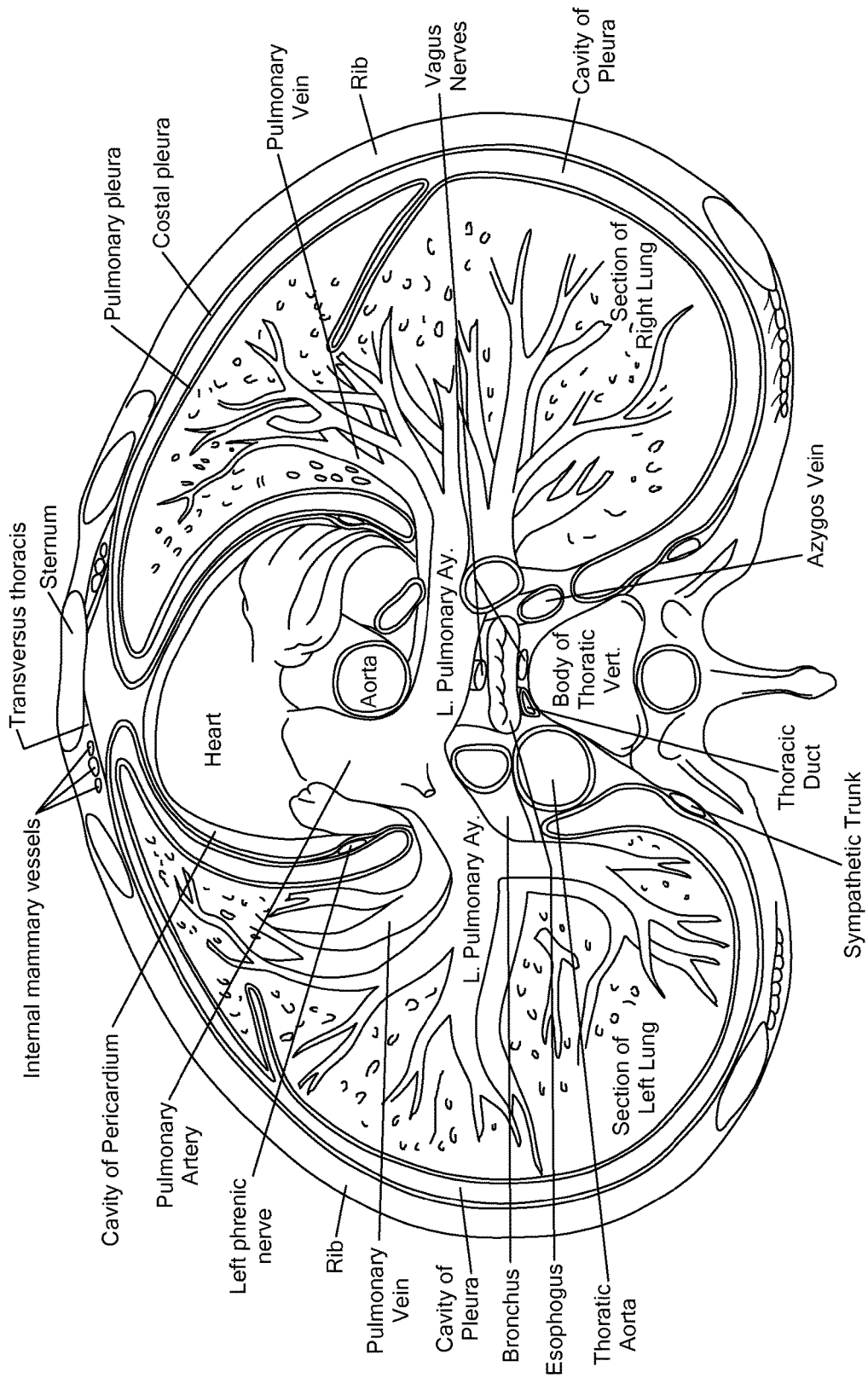
FIG. 3 is an additional illustration of a human heart and related anatomy.
Figure 4:
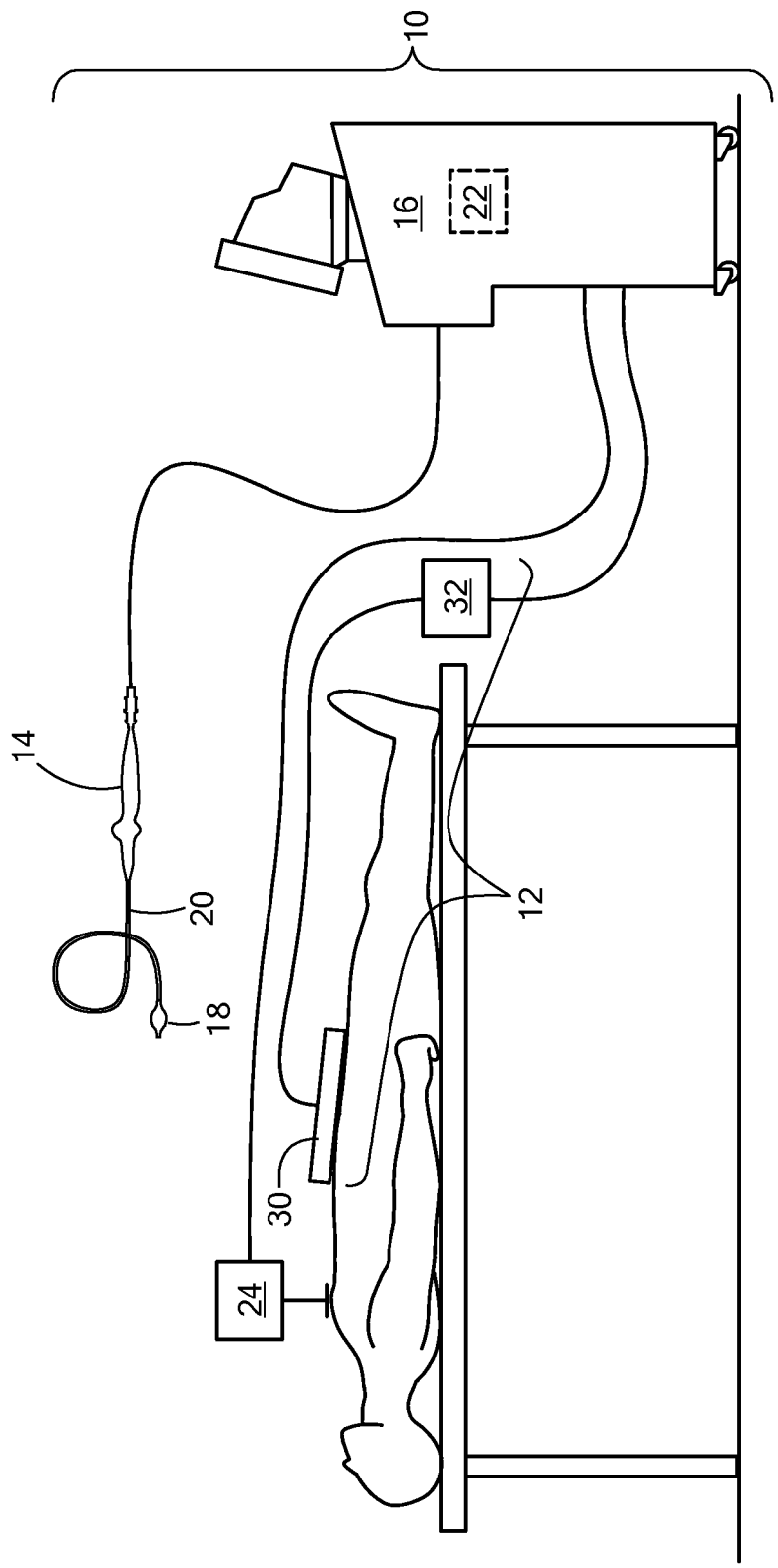
FIG. 4 is an illustration of an example of a medical system constructed in accordance with the principles of the present disclosure.

The present invention advantageously provides methods and systems to monitor or otherwise detect potentially-damaging consequences during treatment of sensitive tissue areas. In particular, as shown in the accompanying figures in which like reference designators refer to like components, a medical system is shown in FIG. 4, generally designated as '10'. The medical system 10 may generally include a diaphragm monitoring or assessment device 12, a medical diagnostic or treatment device 14, and one or more control units 16 coupled to the diaphragm monitoring device 12 and/or the medical treatment device 14.

The tissue treatment/diagnostic device 14 may include a medical probe, a catheter, or other instrument, and may generally include one or more diagnostic or treatment regions 18 for energetic or other therapeutic interaction between the medical device and a treatment site. The treatment region(s) 18 may deliver, for example, cryogenic therapy, radiofrequency energy, or other energetic transfer with a tissue area in proximity to the treatment region(s), including cardiac tissue. The diagnostic or treatment region(s) 18 may include, for example, one or balloons or other thermally and/or electrically-conductive components, such as one or more electrodes in communication with the control unit 16.

The medical device 14 may include an elongate body 20 passable through a patient's vasculature and/or positionable proximate to a tissue region for diagnosis or treatment, such as a catheter, sheath, or intravascular introducer. The elongate body 20 may define a proximal portion and a distal portion, and may further include one or more lumens disposed within the elongate body that provide mechanical, electrical, and/or fluid communication between the proximal portion of the elongate body and the distal portion of the elongate body, which may include the one or more diagnostic or treatment region(s).

The medical device 14 may include a handle coupled to the proximal portion of the elongate body, where the handle may include one or more steering or deflection components for manipulating the catheter body and/or additional components of the medical device 14. The handle may also include connectors that are matable directly or indirectly to the control unit 16 to establish communication between the one or more components of the medical device 14 with one or more components of the control unit 16, as described herein. For example, in an exemplary system, a coolant/fluid supply and exhaust and/or one or more alternative energy sources 22 to supply the selected modality of treatment to the treatment region(s) (such as, for example, a radiofrequency generator, ultrasound generator, light sources, or the like) as well as various control mechanisms for the system 10 may be housed in the control unit 16. The control unit 16 may include one or more controllers, processors, and/or software modules containing instructions or algorithms to provide for the automated operation and performance of the features, sequences, or procedures described herein.

The medical device 14 and/or control unit 16 may include one or more sensors to monitor the operating parameters throughout the system 10, including for example, pressure, temperature, flow rates, volume, or the like in the control unit 16, and/or the medical device 14. For example, the medical device 14 may further include one or more temperature and/or pressure sensors (not shown) proximate the treatment region(s) 18 for monitoring, recording or otherwise conveying measurements of conditions within the medical device 14 or the ambient environment at the distal portion of the medical device 14. The sensor(s) may be in communication with the control unit 16 for initiating or triggering one or more alerts or therapeutic delivery modifications during operation of the medical device 14.

The system 10 may further include the stimulation, measuring and/or monitoring of a physiological condition of a patient, as well as subsequent triggering or actuation of one or more predetermined, automated protocols or procedures in response to the monitored/measured condition. For example, the system 10 may provide for the stimulation of the phrenic nerve via one or more clinical modalities to measure an induced response. As discussed above, the phrenic nerve is a sensitive physiological structure located in the vicinity of cardiac tissue that may be targeted for one or more treatment applications (such as ablation to treat an arrhythmia, for example). The induced response may then be used to establish or otherwise define a threshold or baseline value. Subsequent activity or physiological changes occurring in the patient during a therapeutic procedure may be compared to the baseline or threshold value and thus generate an alert and/or be used to modify one or more parameters of the delivered treatment.

Figure 5:
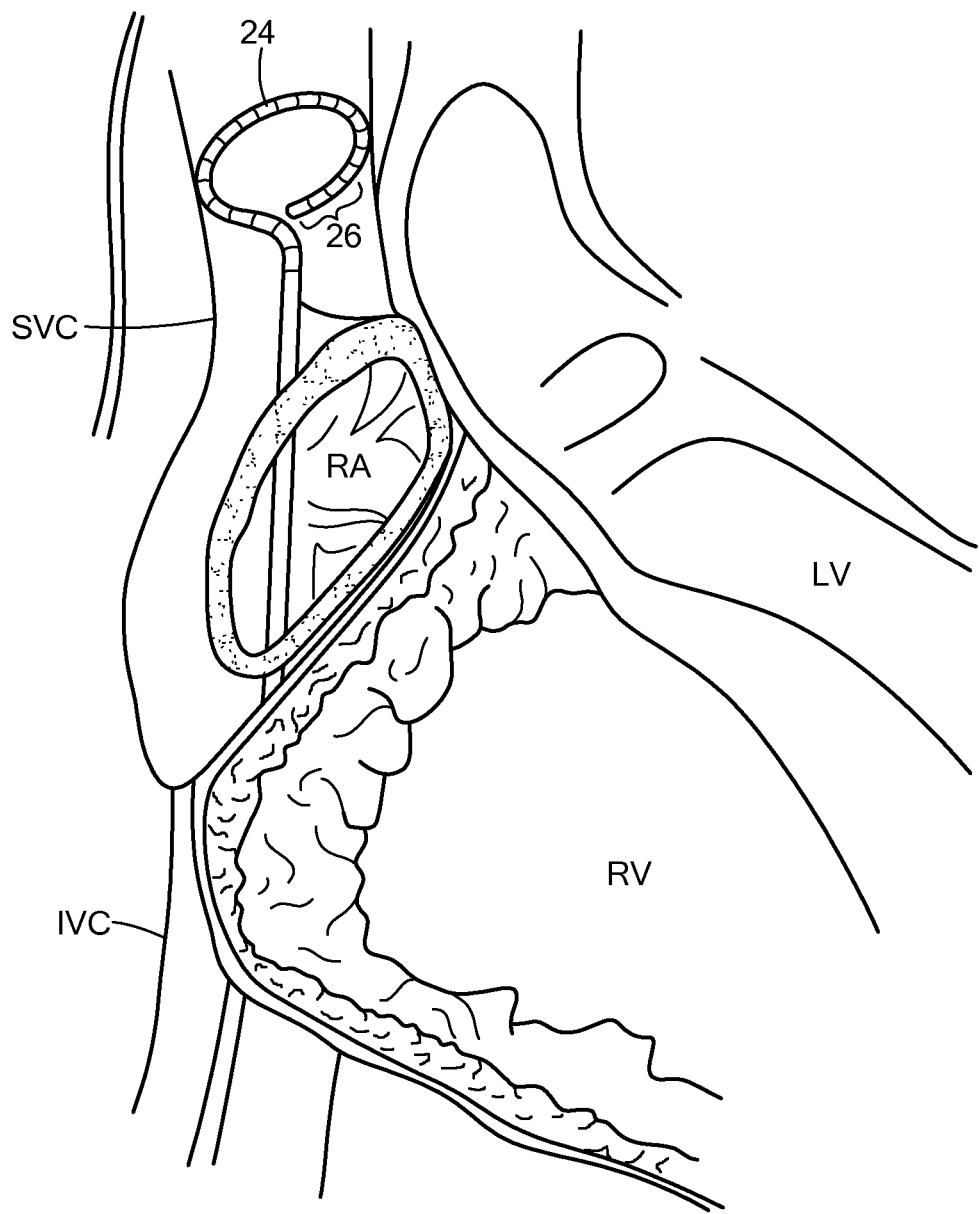
FIG. 5 is an illustration of an example of a stimulation device of the system of FIG. 4.

Now referring to FIG. 4-5, the medical system 10 of the present invention may include a stimulation device 24 for exciting or stimulating a stimulation target tissue area or structure, such as the phrenic nerve, proximal to the ablation site. The stimulation device 24 may provide the controlled delivery of electrical and/or magnetic impulses to the targeted tissue. The stimulation device 24 may include one or more electrically and/or magnetically conductive portions 26 in proximity to the targeted tissue structure for stimulation delivery. For example, one or more electrodes or leads may be positioned on the patient and/or a minimally-invasive or surgical device having conductive elements thereon may be positioned about the stimulation targeted structure (such as the phrenic nerve) to deliver the stimulating pulse or energy, as shown in FIG. 5. The electrodes or electrically/magnetically conducive elements may be coupled to an energy source providing the stimulating energy. A controller and/or processing components may also be included to control, adjust, or otherwise manipulate and select the appropriate energy to be delivered to accomplish the subsequent stimulation or excitation of the targeted tissue structure. The excitation energy source, controller, and/or processor may be housed within or otherwise provided as part of the control unit 16, with the stimulation device 24 being releasably coupled to the control unit 16 during operation thereof.

Figure 6:
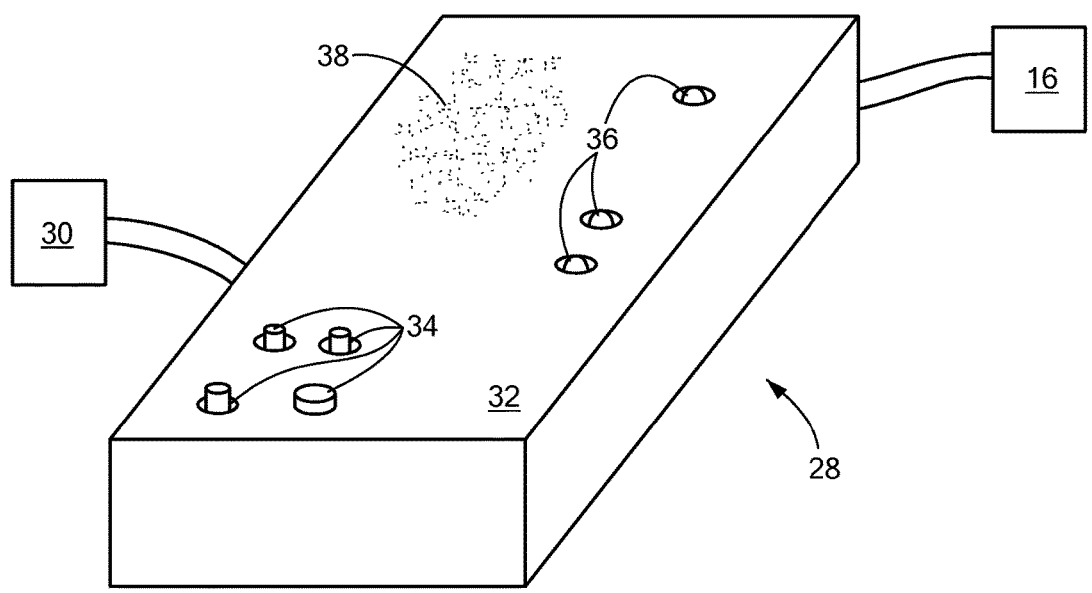
FIG. 6 is an illustration of an example of an assessment device of the system of FIG. 4.

Referring now to FIGS. 4 and 6, the system 10 may include the diaphragmatic or thoracic excursion assessment device 12 for measuring, monitoring, or otherwise assessing movement and/or contraction of the diaphragm or thoracic cavity excursion, which can be used to assess or monitor phrenic nerve function. The assessment device 12 may include one or more sensors 30 to gauge, measure, or monitor diaphragmatic activity, as well as a sensor processor and/or controller unit 32 coupled to and receiving information from the sensors 30. Of note, though the sensor processor/controller unit 32 is illustrated as separate from the control unit 16, it is contemplated that the components and processes performed by the processor/controller unit 32 may be integrated into the control unit 16 itself as a single, multi-functional part of the system 10.

The sensor(s) 30 of the assessment device 12 may include one or more accelerometers providing indications of movement of the diaphragm and thoracic cavity in one or more planes. In a particular example, a 3-axis accelerometer may be included. The implemented accelerometer(s) may operate according to any of a number of sensing methodologies, such as measuring the displacement of a suspended proof mass; measuring piezoresistive effects from movement of a proof mass; and/or by measuring differential capacitive changes by attaching a proof mass to a capacitive plate, for example. The accelerometers may be positioned on or about an external surface of the diaphragm and/or thoracic cavity such that they are operable to detect diaphragmatic movement.

The sensors 30 may include an acoustic transducer or monitoring device, such as a microphone, to monitor acoustic changes or activity on or about the diaphragm. The acoustic measurements may be processed or otherwise used to detect diaphragmatic contraction, which can then be used as an indication of respiratory conditions and correlation to phrenic compromise or injury.

The sensors 30 of the assessment device 12 may monitor or record electromyography ("EMG") measurements of the diaphragm and/or thoracic musculature. An electromyograph detects the electrical potential generated by muscle cells when these cells are both mechanically active and at rest. To perform intramuscular EMG, an electrode may be inserted through the skin into the muscle tissue. Subsequently, electrical signals may be taken upon contraction of the muscle (such as in response to the induced excitation of the targeted tissue structure) and again during relaxation. The shape, size and frequency of the resulting muscle motor unit potentials can then be analyzed to establish a baseline or threshold value for later comparison. In cases where intramuscular EMG may be considered too invasive or unnecessary, a surface electrode may be used to monitor the muscle activation.

Figure 7:
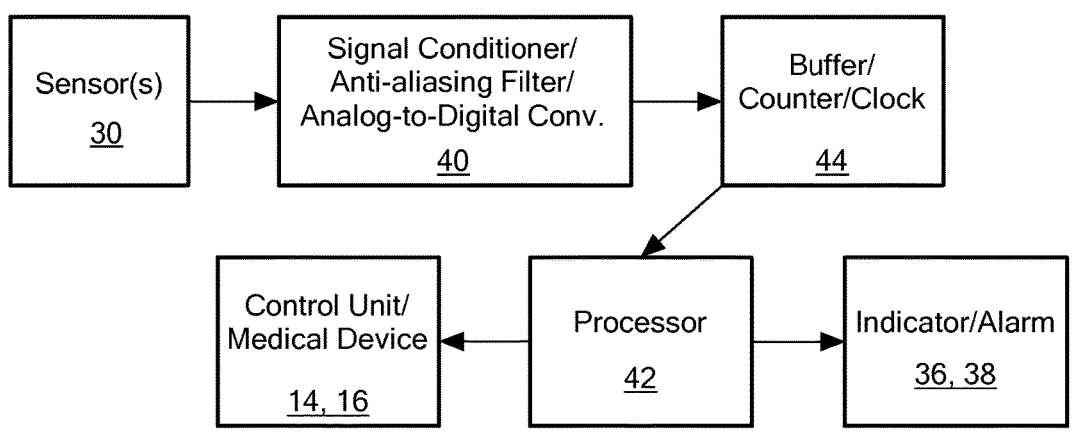
FIG. 7 is a block diagram of the assessment device of FIG. 6.

Now referring to FIGS. 6-7, the sensor processor/controller unit 32 may be in communication with the sensors 30 and/or the control unit 16. The sensor processor/controller unit 32 may include one or more input components 34 (such as buttons, touch screen, or other user interface mechanisms) for the selective operation of one or more features of the sensor processor unit 32, such as powering on the device, resetting an alarm, or the like. The sensor processor/controller unit 32 may also include one or more notification elements 36. For example, one or more visual notification elements may be provided to visually indicate that the sensors and/or processor are operating properly, that one or more alerts have been generated, etc. An audible notification element 38, such as a speaker, may also be include to alert a user that a pre-defined event has occurred and/or that action or modification is warranted.

Turning to FIG. 7, the sensor processor/controller unit 32 may receive the measurements or information from the sensors 30, which may then be conditioned, filtered, and/or otherwise processed 40 and conveyed to one or more processors 42 therein (or in the control unit 16) for analysis and/or comparison. The sensor processor/controller unit 32 may include a buffer and one or more timing components 44 allowing information received from the sensors to be taken at recurring or preselected time periods for continuous monitoring during a given time period, such as a particular medical treatment. The information from the sensors 30 may be further modified or assessed by the processor 42, and the processed information may then be used to determine any appropriate action responsive to the measured characteristics. For example, the processor 42 may directly initiate or generate an alert through an indicator or alarm signaling the physician to adjust or terminate the thermal treatment regimen. The processor 42 may signal or otherwise convey instructions or alerts directly to the control unit 16 and/or medical device 14 to automatically alter the delivery of therapeutic energy or treatment by the medical device 14 in response to the information provided by the sensors. The processor and/or related hardware and software components affecting a predetermined course of action based on the information provided by the sensors 30 and sensor processor/controller unit 32 may be contained within or otherwise provided with the control unit 16. Though the indicators, input components, and processing components of the sensor processor/controller unit 32 are illustrated as separate from the control unit 16, it is contemplated that these components may be integrated into the control unit 16 as well.

Figure 8:
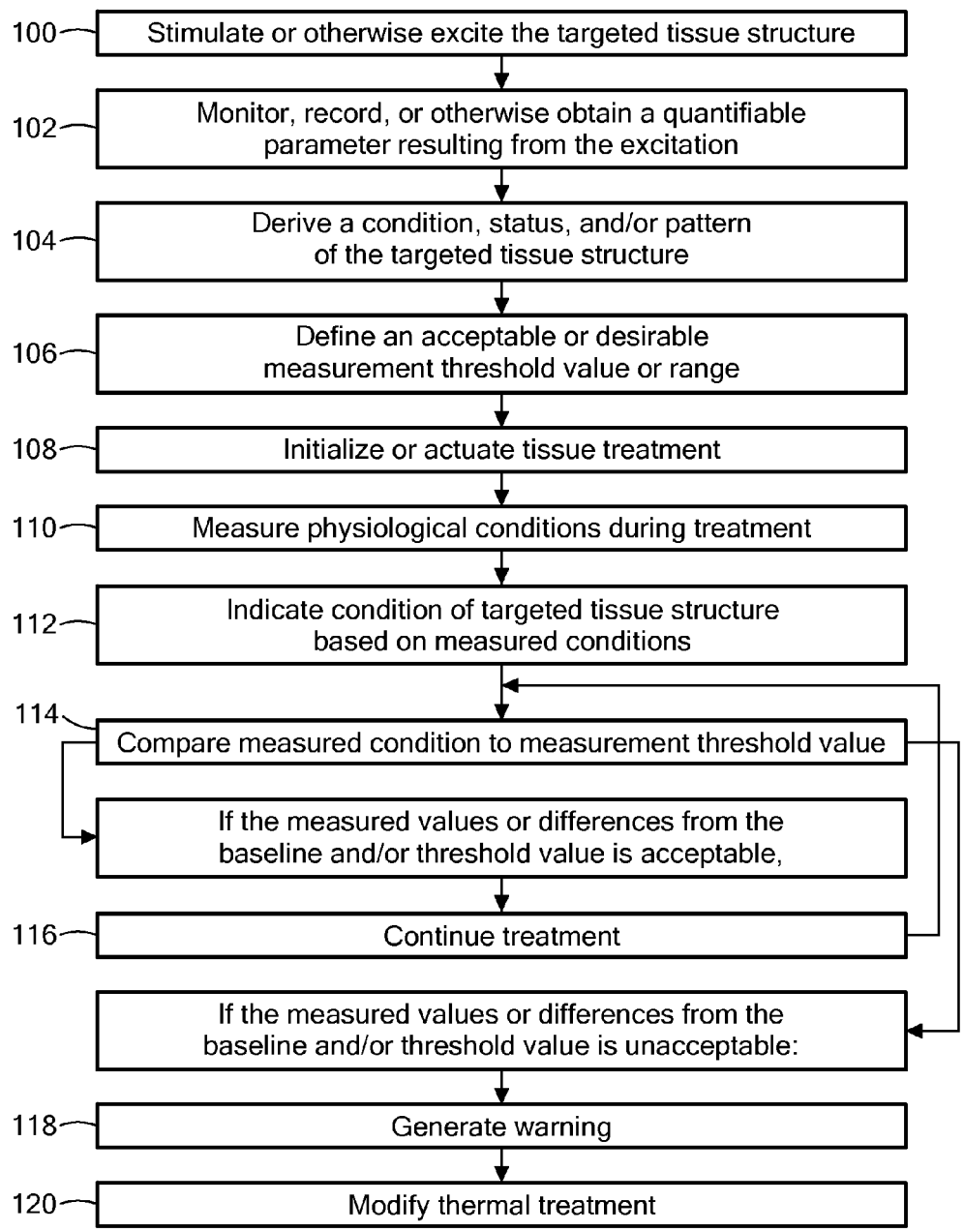
FIG. 8 is a flow chart of an exemplary method of use of the system of FIG. 4.

Now referring to FIG. 8, a method for monitoring tissue function and/or preventing unintended nerve or tissue injury is shown. In a particular example, a method for monitoring phrenic nerve activity during treatment of tissue is shown. The sensors 30 may be positioned in proximity to the diaphragm or thoracic cavity such that the sensors are able to detect or monitor activity of the diaphragm. For example, the sensors 30 may be taped to the skin surface and connected to the sensor controller unit and/or the control unit 16. The stimulation device 24 is positioned to deliver an excitation or simulating energy to at least a portion of the phrenic nerve. For example, the stimulation device 24 may be positioned in the SVC and configured to pace and capture the phrenic nerve. Once positioned, the stimulation device 24 is activated to stimulate or otherwise excite the targeted tissue structure, here being the phrenic nerve, for example (Step 100). The excitation of the targeted structure may be achieved through the delivery of one or more types of excitation energy (such as electrical, magnetic, chemical, or the like) at a predetermined volume, rate, and/or time duration.

Once the physician begins pacing the phrenic nerve, the sensors 30 and sensor processor unit 32 may monitor, record, or otherwise obtain a quantifiable parameter resulting from the excitation (Step 102), such as a detection of diaphragmatic movement that results from the phrenic stimulation, acoustic measurements correlating to diaphragmatic contraction, and/or EMG measurements. The measured values may then be processed by filters, amplifiers, or the like to eliminate artifacts, adjusted for attenuation due to fatigue, etc., and conveyed to a processing unit or component, such as those of the control unit 16 and/or sensor processor/controller unit 32. A condition, status, and/or pattern of the phrenic nerve may then be derived or otherwise indicated (Step 104) based at least in part on the stimulation energy delivered in Step 100 and/or the processed measurements obtained in Step 102. An acceptable or desirable measurement threshold value or range may also be determined or otherwise defined (Step 106).

Figure 9:
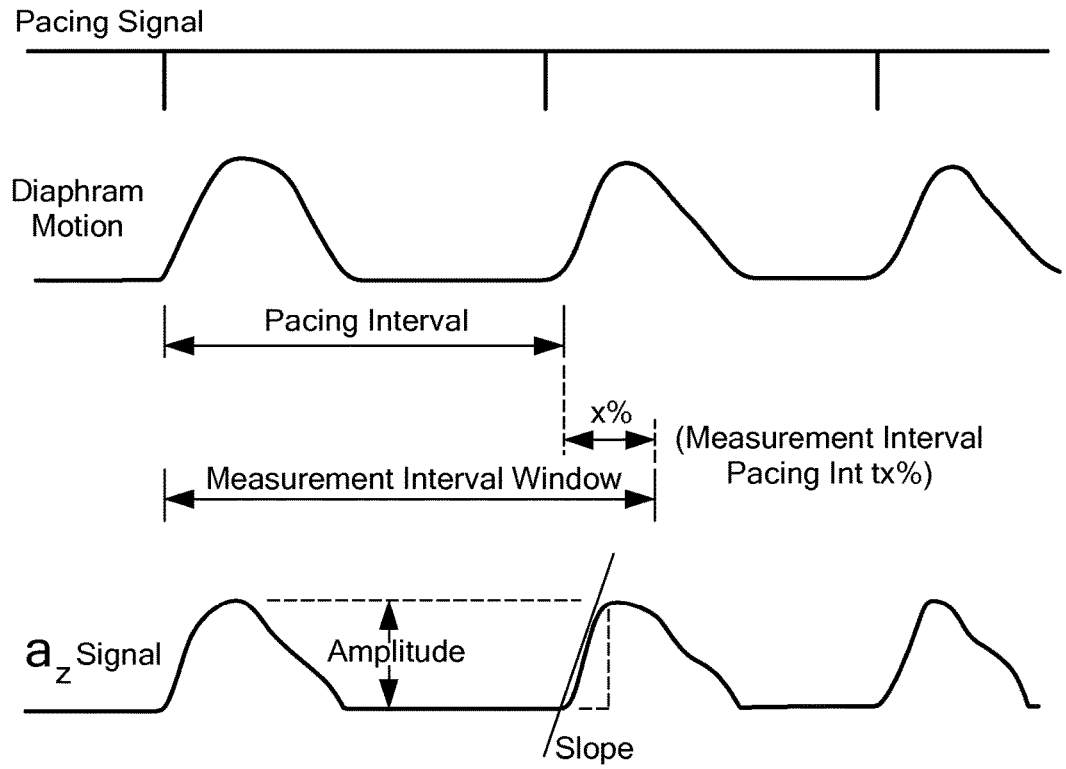
FIG. 9 is an illustration of examples of signals obtained with the system of FIG. 4.

Should the sensors 30 include one or more accelerometers to monitor diaphragmatic movement, this may be accomplished by measuring the frequency of phrenic stimulation (i.e. frequency of abdominal excursions caused by phrenic pacing) and creating a "measurement window" interval slightly longer than the stimulation pulse width by detecting an initial spike (corresponding to a diaphragmatic excursion) and timing the duration to the next spike, as shown in FIG. 9. This period corresponds to the phrenic pacing rate. The sensors 30 and/or sensor processor/controller unit 32 may also measure the slopes and amplitudes of both spikes, using these values to set nominal values for these two parameters.

Once a baseline status or physiological condition has been established, treatment of the selected region of tissue may proceed with the medical device 14 in proximity to the monitored tissue structure, such as the phrenic nerve. In particular, the medical device 14 may be actuated (Step 108). In the case of cryotherapy, this may include delivery of a refrigerant or coolant to the catheter. In the case of radiofrequency, microwave, ultrasound, or the like, actuation may include actuation or initiation of the respective energy transducers on the particular device. The medical device 14 may be operated within sufficient proximity to the monitored tissue structure that the possibility exists that the treatment regimen may adversely affect the monitored tissue. For example, thermal treatments in an endocardial and/or epicardial region of the patient, esophageal treatments, and/or other regions around the phrenic nerve may provide sufficient concern as to warrant monitoring for adverse, unintended nerve effect. A particular example of a targeted cardiac region may include, for example, one or more superior pulmonary veins. Physiological conditions then may be measured at selected interims or continuously by the assessment device during treatment (Step 110).

Figure 10:
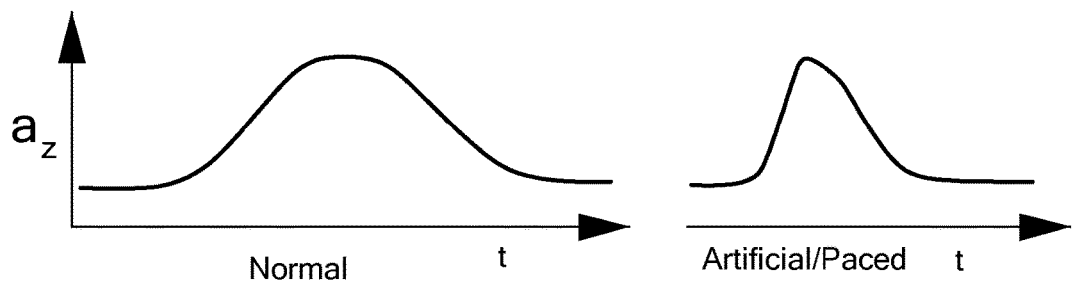
FIG. 10 is another illustration of examples of signals obtained with the system of FIG. 4.
Figure 11:
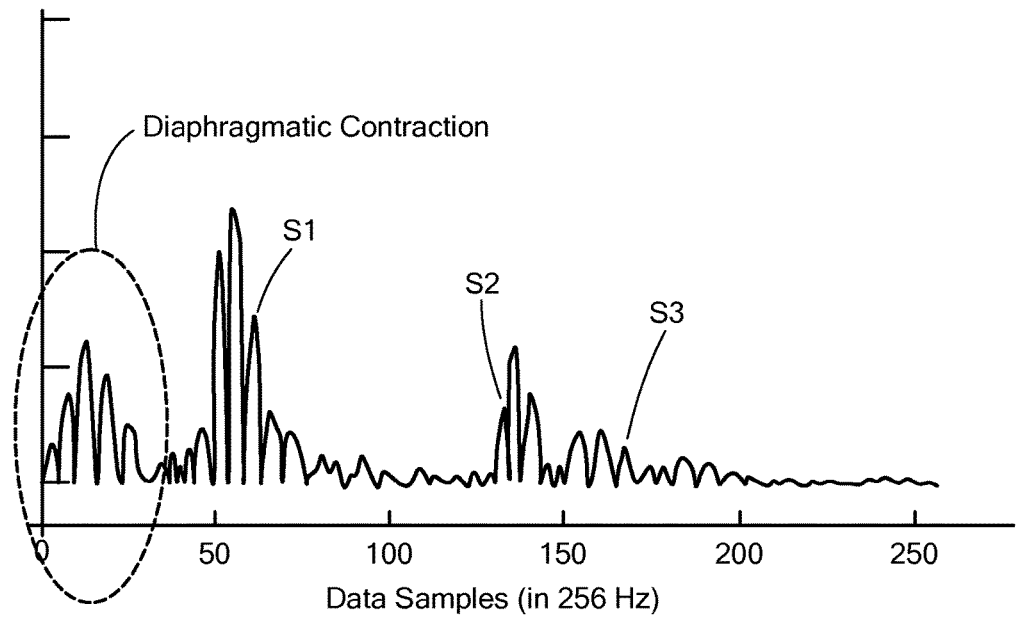
FIG. 11 is another illustration of examples of signals obtained with the system of FIG. 4.

For example, the slope and magnitude of an accelerometer waveform may be measured and compared against subsequent excursions. The paced phrenic nerve creates an artificially fast diaphragmatic excursion relative to natural respiration efforts. FIG. 10 shows an example of a typical excursion-over-time graph of a normal respiration and an accelerated diaphragm response to phrenic pacing. This paced excursion results in a spike in the value of az (and possibly other axes depending on accelerometer placement and orientation). The sensors 30 and/or sensor processor/controller unit 32 may detect this spike and monitor the time between consecutive spikes. This interval corresponds to the phrenic pacing rate. A "missed" spike (i.e. a spike that occurs after the expiration of the measurement window) or an attenuated diaphragmatic motion signal (indicating compromised diaphragm movement) trigger an alert to the operator (or optionally suspend or modulate operation of the medical device 14). In addition and/or alternatively to the accelerometers, acoustic signals received from the sensors 30 may be processed to detect diaphragmatic contraction, as shown in FIG. 11. For example, as shown in FIG.11, the rectified HS waveform over a beat cycle using ventricular pacing marker as reference point with heart rate 60 bpm was illustrated along with heart sounds S1, S2, and S3. The x-axis is in data samples taken at a frequency of 256 Hz, where 0 indicates Ventricular pacing time. The illustrated waveform indicates that the Phrenic Nerve Stimulation (PNS) artifacts within an approximately 80-100 ms window just after Ventricular pacing marker (0 at x-axis), but before heart sounds S1 occur on the HS waveforms.

A current or real-time condition, status, and or pattern of the target structure (the phrenic nerve, for example) may then be derived, correlated, or otherwise indicated from the processed physiological conditions (Step 112). The current measurements may then be compared to the original baseline or threshold values (Step 114). If the measured values or difference from the baseline and/or threshold value is acceptable, treatment may continue (Step 116). If the measured values or difference from the baseline and/or threshold value is unacceptable, a warning may be generated (Step 118) and the thermal treatment may then be modified (Step 120). For example, the treatment may be automatically terminated, may be reduced in intensity, application, or temperature, or otherwise adjusted until the monitored conditions reach acceptable levels with respect to the defined threshold (or range).

Figure 12:
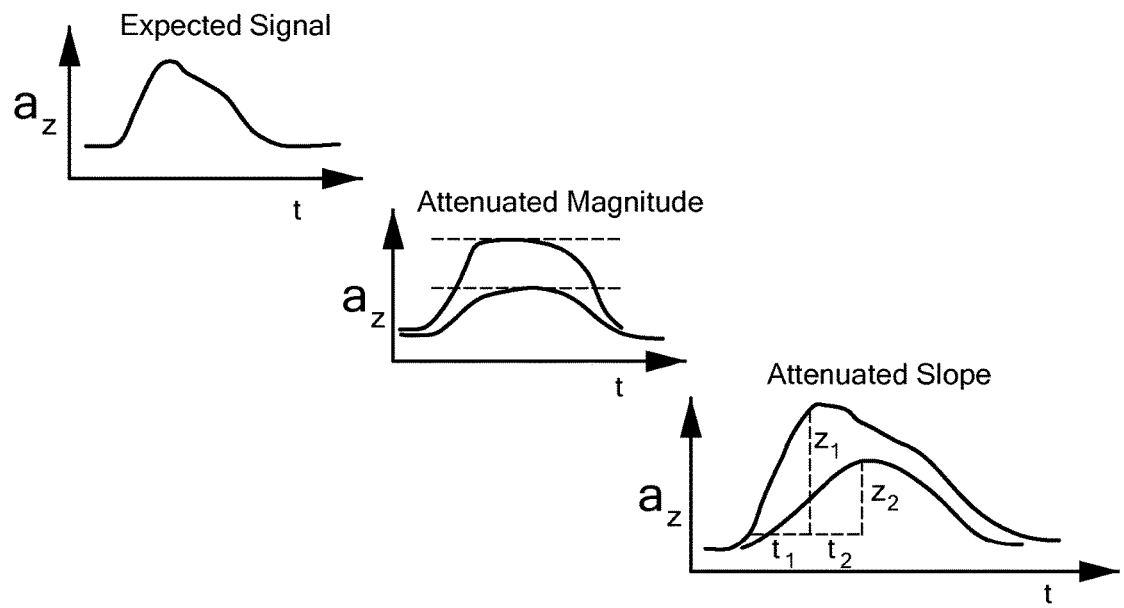
FIG. 12 is an illustration of examples of signals obtained with the system of FIG. 4.

In an example of this particular methodology using one or more accelerometers, the slope and amplitude of each diaphragm excursion is compared to the initial values. For example, the signals from accelerometers may be processed to provide a digital waveform representing motion detected by the sensors. Such waveforms may be further filtered and processed to provide detection of either a missed diaphragmatic excursion or an attenuated diaphragmatic excursion (as shown in FIG. 12), indicating possible phrenic compromise. For example, if a spike is detected within the measurement window, and that spike is of sufficient slope and magnitude, the device resets the measurement window counter and continues monitoring the accelerometer. If the slope declines by x %, or the magnitude decreases x % from normal, or the spike does not occur before the measurement window counter expires, the system 10 triggers the alert. This warns the physician that a diaphragmatic excursion failed to occur, or that the excursion was compromised (presenting as either a low slope waveform or magnitude attenuated waveform), indicating a likely phrenic response to the treatment.

Stimulating a target tissue, such as the phrenic nerve, and subsequently measuring resulting physiological responses provides for a minimally-invasive, non-intrusive method of inferring or otherwise monitoring thermal impact on the phrenic nerve when treating small, sensitive areas of tissue. Phrenic palsy can present as an attenuation of diaphragmatic function. By processing the accelerometer or acoustic signals and identifying changes in the slope of diaphragm response, phrenic attenuation can be detected prior to actual phrenic palsy or injury occurring. Optionally, the assessment device can also automatically disable the administration of therapy from the medical device 14, minimizing the chances of longer-term phrenic injury. By alerting the operator to possible phrenic impairment (manifested by an absence of diaphragmatic excursion), the physician may intervene before phrenic injury occurs, reducing procedural risk and potential patient sequelae. The monitoring provides an additional safeguard to prevent unintentional damage and/or disruption of cursory physiological structures and functions when treating maladies such as cardiac arrhythmias. By providing a system that automatically watches for phrenic attenuation or palsy, and audibly alerts the user to potential issues, patient safety is maximized and physician concerns can be alleviated.

It will be appreciated by persons skilled in the art that the present invention is not limited to what has been particularly shown and described herein above. In addition, unless mention was made above to the contrary, it should be noted that all of the accompanying drawings are not to scale. A variety of modifications and variations are possible in light of the above teachings without departing from the scope and spirit of the invention, which is limited only by the following claims.

What is claimed is:

1. A method of monitoring phrenic nerve function of a patient during a treatment regimen, the method comprising:
positioning a motion sensor including an accelerometer on an external surface of the patient in proximity to a diaphragm of the patient;
delivering excitation energy to a phrenic nerve of the patient by a stimulation device;
measuring with the accelerometer a slope of amplitude over time of a pre-treatment diaphragm excursion in response to the delivery of excitation energy to the phrenic nerve and an amplitude of a pre-treatment diaphragm excursion in response to the delivery of excitation energy to the phrenic nerve;
establishing a pre-treatment slope of amplitude over time threshold and a pre-treatment amplitude threshold, the pre-treatment slope of amplitude over time threshold and the pre-treatment amplitude threshold being based on one of the pre-treatment slope of amplitude over time and the pre-treatment amplitude;
applying the treatment regimen to a tissue region in proximity to the phrenic nerve with a treatment device;
measuring with the accelerometer an in-treatment slope of amplitude over time and an in-treatment amplitude of an in-treatment diaphragm excursion;
comparing the measured in-treatment slope of amplitude over time and the measured in-treatment amplitude to the established pre-treatment slope of amplitude over time threshold and the established pre-treatment amplitude threshold, the comparison indicating phrenic nerve impairment when at least one of the in-treatment slope of amplitude over time and the in-treatment amplitude is less than the slope of amplitude over time threshold or the amplitude threshold; and
generating an alert when the comparison indicates phrenic nerve impairment.

2. The method of claim 1, further comprising:
establishing a diaphragm electromyogram threshold;
obtaining an electromyogram of the diaphragm;
comparing the obtained electromyogram to the established diaphragm electromyogram threshold; and
generating an alert based at least in part on the comparison.

3. The method of claim 1, wherein the treatment regimen includes ablating cardiac tissue.

4. A medical system for monitoring phrenic nerve function of a patient during a treatment regimen, the medical system comprising:
a motion sensor positionable on an exterior surface of a patient, the motion sensor including an accelerometer;
a stimulation device configured to deliver at least one of electric and magnetic impulses to the patient's phrenic nerve;
a treatment device configured to deliver treatment energy to a target tissue site proximate the patient's phrenic nerve; and
a controller in communication with the motion sensor and the stimulation device, the controller programmed to:
transmit at least one of electric and magnetic impulses to the stimulation device, the stimulation device delivering the at least one of electric and magnetic impulses to the patient's phrenic nerve in a plurality of stimulation pulses to cause a plurality of diaphragm excursions, each of the diaphragm excursions having a peak amplitude;
determine a pacing rate based on the delivery of the plurality of stimulation pulses, the pacing rate being a time interval between peak amplitudes of a first diaphragm excursion and a second diaphragm excursion;
establish a measurement time interval for each of the plurality of stimulation pulses, the measurement time interval for each of the plurality of stimulation pulses being longer than the pacing rate;
determine whether a diaphragm excursion is produced during each measurement time interval as a result of delivery of each of the plurality of stimulation pulses;
generate a first alert when the controller determines an absence of a diaphragm excursion during the measurement time interval, an absence of a diaphragm excursion indicating phrenic nerve impairment;
calculate a threshold slope and a threshold amplitude of a pre-treatment diaphragm excursion based on a signal received from the accelerometer in response to the delivery of the plurality of stimulation pulses;
transmit treatment energy to the treatment device, the treatment device delivering the treatment energy to the target tissue site;

calculate an in-treatment slope and an in-treatment amplitude of a diaphragm excursion based on a signal received from the accelerometer;

compare the in-treatment slope and the in-treatment amplitude to the threshold slope and the threshold amplitude, the comparison indicating phrenic nerve impairment when at least one of the in-treatment slope and the in-treatment amplitude is less than the threshold slope or the threshold amplitude;

generate a second alert when the comparison indicates phrenic nerve impairment; and modify delivery of treatment energy when the comparison indicates phrenic nerve impairment.

5. The medical system of claim 4, wherein the motion sensor includes a plurality of accelerometers.

6. The medical system of claim 4, wherein the each of the first alert and the second alert is at least one of an audible or visual alert.

7. The medical system of claim 4, further comprising a tissue treatment device in communication with the controller.

8. The medical system of claim 7, wherein the controller is programmed to modify operation of the tissue treatment device based at least in part on the comparison.

* * * * *